United States Patent
Kim et al.

(10) Patent No.: US 7,951,572 B2
(45) Date of Patent: May 31, 2011

(54) CONSTRUCTION OF GOLD NANOPARTICLE-BASED PEPTIDE CHIP, AND ASSAYING ENZYME ACTIVITY AND INHIBITOR EFFECT USING SECONDARY ION MASS SPECTROMETRIC ANALYSIS THEREOF

(75) Inventors: Hak-Sung Kim, Daejeon (KR); Young-Pil Kim, Daejeon (KR); Eunkeu Oh, Daejeon (KR); Mi-Young Hong, Daejeon (KR); Dohoon Lee, Seoul (KR); Tae Geol Lee, Daejeon (KR); Dae Won Moon, Daejeon (KR)

(73) Assignees: Korea Advanced Institute of Science and Technology, Daejeon (KR); Korea Research Institute of Standards and Science, Daejeon (KR)

( * ) Notice: Subject to any disclaimer, the term of this patent is extended or adjusted under 35 U.S.C. 154(b) by 449 days.

(21) Appl. No.: 11/711,036

(22) Filed: Feb. 27, 2007

(65) Prior Publication Data
US 2008/0076676 A1    Mar. 27, 2008

(30) Foreign Application Priority Data
Feb. 27, 2006    (KR) .................. 10-2006-0018603

(51) Int. Cl.
*C12N 9/50*    (2006.01)
*C07K 5/00*    (2006.01)
(52) U.S. Cl. ........ 435/219; 435/212; 435/183; 435/174; 435/4; 506/13
(58) Field of Classification Search .................. 435/219, 435/212, 183, 174, 4; 506/13
See application file for complete search history.

(56) References Cited

U.S. PATENT DOCUMENTS

| | | | |
|---|---|---|---|
| 5,874,219 A | 2/1999 | Rava | 435/6 |
| 6,469,151 B1 | 10/2002 | Egholm | 536/23.1 |
| 6,703,203 B2 | 3/2004 | Shao | 435/6 |
| 6,887,713 B2 * | 5/2005 | Nelson et al. | 436/173 |
| 7,235,389 B2 | 6/2007 | Lim | 435/174 |
| 7,417,183 B1 | 8/2008 | Short | 800/320.1 |
| 7,442,773 B2 | 10/2008 | Zhao | 530/387.1 |

OTHER PUBLICATIONS

McLean et al, Jrnl. Am. Chem. Soc. 2005, 127, 5304-5305.*
Ehler et al, J. Phys. Chem. B, 1997, 101,1268-1272.*
Analytical Chemistry Web release Date Feb. 7, 2006 http://pubs3.acs.org/acs/journals/supporting_information.page?in_manuscript=ac051500j.
Young-Pil Kim et al. "Gold Nanoparticle-Enhanced Secondary Ion Mass Spectrometry Imaging of Peptides on Self-Assembled Monolayers" American Chemical Society Published on Web, Feb 7, 2006. pp. A-H.

* cited by examiner

*Primary Examiner* — Teresa D. Wessendorf
(74) *Attorney, Agent, or Firm* — Staas & Halsey LLP (57) ABSTRACT

Disclosed herein is a gold nanoparticle (AuNP)-based peptide chip prepared by forming a monolayer of AuNPs onto a self-assembled monolayer constructed on a solid support, and then immobilizing a peptide on the AuNPs. The AuNPs can effectively amplify the mass signal of the peptide, thus making it possible to measure the mass change of the peptide in a simple and accurate manner. Also, when secondary ion mass spectrometric analysis (spectrum or imaging) is performed on the AuNP-based peptide chip, the activities of enzymes and related inhibitors can be effectively quantified. The disclosed invention enables various enzyme activities to be analyzed rapidly and accurately, and thus can provide an important method for disease diagnosis and new drug development through the elucidation of signaling and interaction mechanisms.

1 Claim, 5 Drawing Sheets

CONSTRUCTION OF GOLD NANOPARTICLE-BASED PEPTIDE CHIP, AND ASSAYING ENZYME ACTIVITY AND INHIBITOR EFFECT USING SECONDARY ION MASS SPECTROMETRIC ANALYSIS THEREOF

BACKGROUND OF THE INVENTION

This application claims priority from Korean Patent Application No. 10-2006-0018603 filed on Feb. 27, 2006 in the Korean Intellectual Property Office, the disclosure of which is incorporated herein by reference in its entirety.

FIELD OF THE INVENTION

The present invention relates to a gold nanoparticle-based peptide chip and methods for detecting and measuring enzyme activity using the enhanced secondary ion mass signal of peptide on the gold nanoparticle monolayer. Furthermore, the present invention relates to methods of using the gold nanoparticle-based peptide chip to screen inhibitors against enzyme activity and to measure the inhibitory activity thereof.

BACKGROUND OF THE RELATED ART

Evaluating the activity of various enzymes is essential for understanding of cellular mechanisms, such as intracellular signaling, division and growth processes. For example, the antagonistic interactions between kinase and phosphatase, which are involved in post-translational modifications, are closely associated with various disease-related signaling pathways in cells (Hunter, T., Cell, 100, 113-127). Generally, methods of measuring enzymatic activity are performed through antigen-antibody reactions in solution, such as the enzyme-linked immunosorbent assay (ELISA), but chip-based methods have recently been introduced for high-throughput analysis (MacBeath, G. and Schreiber, S. L. 2000, Science, 289, 1760-1763). In particular, a peptide chip has been popularly employed as a screening method of enzyme activity, due to the functional stability, facile synthesis of the substrate, and reproducible binding affinity (Reimer, U., Reineke, U. and Schneider-Mergener, J. Cur. Opi. Biotech. 2002, 13, 315-320). However, the peptide chip also depends mainly on fluorescence or radioisotope-labeled methods in the final analysis step, which are still time-consuming and labor-intensive.

In this regard, mass spectrometry allows for significant applicability for enzyme assay as a non-labeling method, when it is applied to the peptide chip, because it can provide a more accurate and precise method by directly detecting the mass change of peptide.

Widely used mass spectrometry includes electrospray ionization mass spectrometry (ESI-MS) and matrix-assisted laser desorption/ionization mass spectrometry (MALDI-MS). Technology of applying mass spectrometry to the chip surface typically involves surface-enhanced laser desorption/ionization (SELDI) spectrometry, and the Mrksich's group carried out mass spectrometry for measuring enzymatic activity and screening an inhibitor on the peptide chip using MALDI (Su, J. and Mrksich, M. Angew, Chem. 2002, 114, 4909-4912; D.-H., Tang, W-J. and Mrksich, M. 2004, Nanobiotech. 22, 717-723). Recently, secondary ion mass spectrometry (SIMS) has been known to be suitable for reproducible analysis in the low mass range, because it has an advantage to analyze the surface without the use of matrix, unlike MALDI. Also, SIMS has been reported to provide very high accuracy and sensitivity at the top layer of 10-15 Å. (Belu, A. M., Graham, D. J. and Castner, D. G. 2003, Biomaterials, 24, 3635-3653). Furthermore, SIMS is known to be very effective in mass spectrometric imaging together with rapid scanning (Altelaar, A. F. M., van Minnen, J., Jimenez, C. R., Heeren, R. M. A. and Piersma, S. R. 2005, Anal. Chem. 77, 735-741), and thus when SIMS is applied to the peptide chip, the applicability thereof will be greatly increased.

However, SIMS has encountered difficulty in directly detecting biomolecules on the chip surface due to a limited mass measurement range (usually less than 200 Da), and various methods for enhancing secondary ion efficiency have been suggested to overcome this difficulty (Wu, K. J.; Odom. R. w. 1996, Anal. Chem. 68, 873-882; McArthur, S. L.; Vendettuoli, M. C., Ratner, B. D. and Caster, D. G., 2004, Langmuir 20, 3704-3709). For example, methods of increasing secondary ion efficiency through cationization by alkali ions or through the application of a thin gold layer have been introduced and there have recently been efforts to increase secondary ion efficiency using a polyatomic ion gun, but these methods still encounter many difficulties in direct application to the peptide chip, due to low ability to improve signals and lack of surface reproducibility. Thus, in order to enhance the utility of the peptide chip, an effective signal amplification method in SIMS, together with a more convenient and reproducible surface construction, is required.

Recently, gold nanoparticles (AuNPs) have been applied in various bioengineering fields. Particularly, in the field of mass spectrometry, there has recently been an example in which AuNPs were used as effective matrixes in MALDI (McLean, J. A., Stumpo, K. A. and Russel, D. H. 2005, J. Am. Chem. Soc. 127, 5304-5305). However, this example comprises mixing the gold nanoparticles with a target analyte in solution and then performing measurements on the surface and is not an example in which AuNPs are applied directly on the chip surface. The case of the aforementioned Mrksich's group comprises performing measurements using the MALDI matrix and is not an example of applying nanoparticles. Examples of applying nanoparticles directly on the chip surface consist of either LSPR (localized surface plasmon resonance) similar to SPR (surface plasmon resonance) (Nath, N. and Chilkoti, A. 2004, Anal. Chem. 76. 5370-5378), or SERS (surface-enhanced Raman scattering) of using the AuNPs as amplified markers (He. L., Natan, M. J. and Keating, C. D. 2000, Anal. Chem. 72, 5348-5355; Cao, Y. C., Jin, R. Nam, J. M., Thaxton, C. S, and Mirkin, C. A. 2003, J. Am. Chem. Soc. 125, 14676-14677). However, there have been no examples so far for applying nanoparticle-based peptide chip to mass spectrometric analysis.

SUMMARY OF THE INVENTION

The present invention has been made in order to solve the above-described problems occurring in the prior art, and it is an object of the present invention to provide a gold nanoparticle-based peptide chip capable of effectively amplifying the mass signal of peptide through secondary ion mass spectrometry.

Another object of the present invention is to provide a method capable of accurately measuring the mass of peptide using the gold nanoparticle-peptide chip without labeling.

Still another object of the present invention is to provide a method of directly measuring enzyme activity using the gold nanoparticle-based peptide chip.

Yet another object of the present invention is to provide a method of screening inhibitors against enzyme and quantifying the inhibitory activities.

Yet still another object of the present invention is to provide a gold nanoparticle-based peptide chip, which can simultaneously analyze the activities of various enzymes through secondary ion mass spectrometric imaging.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 2 discloses "IYAAPKKGGGGC" as SEQ ID NO: 8.;

DETAILED DESCRIPTION OF THE PREFERRED EMBODIMENT

To achieve the above objects, in one aspect, the present invention provides a gold nanoparticle-based peptide chip comprising: (A) a support selected from the group consisting of glass, silicon, metal, semiconductor and plastic; (B) a self-assembled monolayer formed on the surface of the support; (C) a monolayer of gold nanoparticles formed on the self-assembled monolayer through the binding between the terminal group of the self-assembled monolayer and the surface functional group of the gold nanoparticles; and (D) a peptide immobilized by the gold nanoparticles.

The self-assembled monolayer (SAM) is a regularly aligned organic molecular layer covering the surface of the support and can be prepared using alkanoic acid forming ionic bonds with the support, an organosulfur compound forming charge-transfer complexes with the support, or an organosilicon compound forming pure covalent bonds with the support. Specific examples of the compounds forming the self-assembled monolayer may include n-alkanoic acid ($C_nH_{2n+1}COOH$), alkyl silanes, such as alkylchlorosilanes, alkylalkoxysilanes and alkylaminosilanes, and organosulfur compounds, such as alkylthiolates, n-alkyl sulfide, di-n-alkyl disulfide, thiophenols, mercaptopyridines, mercaptoanilines and mercaptoimidazoles, wherein each of the compounds preferably has 3-25 carbon atoms.

Generally, the compounds forming the self-assembled monolayers consist of a reactive group in the head portion, which binds to the substrate, a long alkane chain in the body portion, which allows the formation of regular molecular layers, and a functional group in the terminal portion, which determines the function of the molecular layers. The functional group in the terminal portion can be exemplified by an alkyl group as the simplest functional group and can preferably be one or a mixture of two or more selected from among amine, thiol, carboxy, aldehyde, epoxy and maleimide.

The self-assembled monolayer is formed by preparing a solution containing the compound in a concentration range of 2-10 mM and then immersing the support in the solution. Herein, an oxide layer on the support surface is preferably removed before the immersion, and a reaction in the process of forming the self-assembled monolayer is preferably performed in a nitrogen atmosphere in order to block an oxidation reaction caused by oxygen in air. The oxide layer on the support can be removed by treating the support with a Pirana solution of sulfuric acid/hydrogen peroxide for 5-10 minutes. The reaction process of the compound for forming the self-assembled monolayer is preferably carried out at room temperature for 2-24 hours, but even if the reaction time exceeds 24 hours, a problem does not arise in the formation of the self-assembled monolayer. To induce a faster reaction, the compound may react at 30-40° C. only for 2 hours.

After the formation of the self-assembled monolayer, the monolayer of gold nanoparticles is formed by preparing a dispersion of gold nanoparticles and then linking the gold nanoparticles in the dispersion to the support surface to form a monolayer. The dispersion of gold nanoparticles can be prepared by dissolving each of a gold salt and a ligand in a suitable solvent, mixing the two solutions with each other, and stirring the mixture, such that the ligand surrounds the metal core to stabilize the gold nanoparticles (Handley, D. E. In Colloidal Gold-Principles, Method, and Applications; Hayat, M. A., Ed.; Academic Press: New York, 1989; Vol 1, Chapter 2, 13-32). As the gold salt, it is possible to use one conventionally used in the preparation of a gold nanoparticle dispersion, for example, $HAuCl_4$ or $NaAuCl_4$, and as the ligand, it is possible to use one or a mixture of two or more selected from the group consisting of citrate, n-alkanethiol, PEG-thiol (polyethyleneglycol thiol), dendrimer, alkylphosphine, alkylphosphine oxide, sulfur-containing ligands ($H_2S$, $(trimethylsilyl)_2S$, xanthate, disulfide, dithiol, trithiol, resorcinarene tetrathiol), $(trimethylsilyl)_3P$, aryl isocyanine, acetone, iodine, PEG and starch.

The binding of gold nanoparticles to the self-assembled monolayer is achieved through the ionic bonding, thiol adsorption or covalent bonding between the terminal group of the self-assembled monolayer and the surface functional group of the gold nanoparticles. In this embodiment, the ionic bonding between anionic gold nanoparticles and an amine-terminated self-assembled monolayer in a neutral solution is illustrated, but the present invention is not limited thereto. After the self-assembled monolayer is formed on the support, the gold nanoparticle monolayer is formed by spraying the gold nanoparticle dispersion on the monolayer surface or immersing the monolayer surface in the gold nanoparticle dispersion. After the reaction is performed at room temperature for 30 minutes or at 4° C. for 1-2 hours, the surface is washed with distilled water. If the reaction time at room temperature is long, the gold nanoparticle dispersion can be coagulated, and for this reason, it is preferable to avoid a reaction for more than 1 hour. To maintain a more reproducible surface, it is preferable to use a method of causing the gold nanoparticle dispersion to flow on the monolayer surface at a given flow rate.

The gold nanoparticles preferably have a size of 1-50 nm. If the size of the gold nanoparticles becomes larger, the repulsive force between the gold nanoparticles will be increased, and thus the density (the number of gold nanoparticles attached per unit area) will be reduced, making it difficult to expect the effect of the gold nanoparticles. The size of gold nanoparticles in a dispersion prepared in Example of the present invention was measured with an electronic microscope and, as a result, the gold nanoparticles had a size of about 3.2 nm (SD±0.4, n=100) and maintained stability at 4° C. for a few days. Also, the gold nanoparticle dispersion bound to the surface of the amine-terminated self-assembled monolayer was analyzed with an atomic force microscope (AFM) and, as a result, it could be seen that the bound gold nanoparticles were uniformly distributed with the same size as that of the gold nanoparticles synthesized in the dispersion (data not shown).

The characteristics (e.g., length, sequence and mass) of peptide are optional particulars that can be suitably selected according to the intended use of the gold nanoparticle-peptide chip, and the present invention is not limited to a peptide having a specific sequence.

In Examples of the present invention, the ionic binding between gold nanoparticles having surface anionic charges and the amine group of the peptide, or the binding by thiol adsorption using the cystein of peptide, was used, but the present invention is not limited thereto and it is possible to use physical adsorption, thiol adsorption, covalent binding, hydrophobic binding and the like depending on the aspect of peptide and gold nanoparticles used. As reaction solvents for this binding, hydrophilic solvents, such as pure distilled water or buffers (e.g., PBS, HEPES, Tris buffer, etc.), and organic solvents, such as DMSO and ethanol, can be used, but a 10-100 mM PBS or HEPES solution maintained at the neutral pH (6-7) range is preferably used. Among them, the Tris solution having an amine group can interfere with the adsorption of peptide by acting on the gold nanoparticle surface having anionic charges. If DMSO is used due to the solubility of peptide in water, the final concentration of DMSO should not exceed 5% (v/v).

The reaction with the gold nanoparticles is carried out by immersing the gold nanoparticle-self assembled monolayer in the peptide solution at room temperature or 4° C. for 0.5-2 hours.

If there is an empty space between the gold nanoparticles in the monolayer formed of the gold nanoparticles, the non-specific adsorption between the self-assembled monolayer and an enzyme can occur in a subsequent secondary reaction. If a functional group, such as amine, thiol, carboxy, aldehyde, epoxy or maleimide, which forms the terminal portion of the self-assembled monolayer, is exposed without binding to the gold nanoparticles, adsorption resulting from either ionic binding with the polar portion of the enzyme or hydrophobic binding with the non-polar portion of the enzyme can occur, and thus it is preferable to fill the space between the gold nanoparticles to prevent non-specific binding. The empty space between the gold nanoparticles is preferably filled with at least one compound selected from the group consisting of ethyleneglycol-based compounds, such as ethyleneglycol amine, ethyleneglycol thiol, N-hydroxysuccinimide (NHS)-ethyleneglycol and maleimide-ethyleneglycol, polyethyleneglycol-based compounds, such as polyethyleneglycol amine, polyethyleneglycol thiol, (NHS)-polyethyleneglycol and maleimide-polyethyleneglycol, and biological compounds, such as carbohydrate unit-based polymers, protein disulfide isomerase, and bovine serum albumin.

The filling of the empty space between the gold nanoparticles is preferably carried out after binding the peptide to the gold nanoparticle monolayer. If the filling process is carried out before the peptide binding, the gold nanoparticle surface can be previously covered so as to interfere with the binding of peptide ligands. More specifically, after the gold nanoparticle monolayer is formed, it is sprayed with or immersed in the solution of the aforementioned compound. The solvent, pH, buffer and the like can be determined depending on the reactivity and solubility of the compound, but a buffer solution having a pH of 5-9 within a range that does not influence the gold nanoparticles and peptide attached to the support surface is suitable compared to organic solvents, and the concentration of the compound is preferably maintained at 2-10 mM.

Another aspect of the present invention relates to a method of measuring the mass of peptide by mass spectrometry using the gold nanoparticle-peptide chip according to the present invention.

As a primary ion source usable in the present invention, any one selected from various ion sources, including As, Ga, Au, Bi and $C_{60}$, and the magnitude of signal amplification can be determined depending on the kind of the primary ion source.

The gold nanoparticle-peptide chip according to the present invention effectively amplifies the mass signal of peptide in secondary ion spectrometry, and thus is effective in measuring the mass of peptide. In order to examine the effect of the gold nanoparticles on the amplification of mass signal of the peptide in the inventive gold particle-peptide chip, the mass signal of peptide on various self-assembled monolayers having no gold nanoparticles was compared with the mass signal of the peptide in the gold nanoparticle-peptide chip. As a result, an about 10-fold increase in signals compared to the case having no gold nanoparticles could be observed, and this was much more effective than a self-assembled monolayer having an aromatic ring structure, which was reported to be more effective for the amplification of secondary ion signals (Vendettuoli, M. C., Ratner, B. D., Castner, D. G., 2004, Langmuir 20, 3704-3709). Furthermore, it was found that this signal amplification effect was not a concentration effect resulting from the difference in the density of the peptide and was an effect resulting from the gold nanoparticles. Thus, when the inventive gold nanoparticle-peptide chip and secondary ion mass spectrometric analysis are used, the mass of the peptide can be measured in a more convenient and accurate manner.

Also, although not mentioned in Examples of the present invention, the results of measurement on supports (silicon and glass substrate) other than the gold surface showed the same signal amplification effect as the case of the gold surface. The effect of the gold nanoparticles on the amplification of mass signals can be readily applied to various supports, even though the magnitude of the mass spectrometric signal of the peptide can be different between the supports, because the density of amine terminal groups in the structure of the substrate surface can be changed depending on differences in the supports and the self-assembled monolayers formed on the supports.

For the mass spectrometry of peptide, the mass of peptide in the gold nanoparticle-peptide chip is preferably less than 1,500 Da, but the measurement range of the mass can be enlarged depending on the form and amount of gold nanoparticles formed on the chip surface, because signals can be increased in proportion to the amount of the formed gold nanoparticles.

Still another aspect of the present invention relates to a method of detecting the activity of enzyme, the method comprising the steps of: (1) measuring the mass of peptide in the inventive gold nanoparticle-peptide chip by secondary ion mass spectrometry; (2) allowing the gold nanoparticle-peptide chip to react with an enzyme to be measured for its activity; (3) measuring the mass of the peptide in the gold nanoparticle-peptide chip after completion of the reaction; and (4) measuring the change between the peptide mass measured in the step (1) and the peptide mass measured in the step (3), to determine the activity of the enzyme.

The enzyme may be one or more enzymes selected from the group consisting of kinase, phosphatase, protease, actylase and methylase.

The peptide in the gold nanoparticle-peptide chip for detecting the activity of enzyme is preferably constructed to have a suitable functional group according to the kind of enzyme to be detected. Examples of the peptide include a form in which cystein is attached to any one of the terminal ends of an amine or carboxyl group, a form in which an amine group such as lysine or arginine is attached, and a form consisting only of the amine- or carboxy-terminal ends of a peptide itself. The length of the peptide can be varied depending on the kind of ligand, and can be regulated with an optional linker. More specifically, IYAAPK (SEQ ID NO: 1) as a peptide ligand having reactivity specific for Abl kinase can be used in various forms, including IYAAPKC (SEQ ID NO: 2), CIYAAPK (SEQ ID NO: 3), IYAAPKK (SEQ ID NO: 4), IYAAPKR (SEQ ID NO: 5) and IYAAPKGGGGC (SEQ ID NO: 6), as mentioned above, and can be acetylated at the amine terminal end (Ac-IYAAPK (SEQ ID NO: 1)), or can be aminated at the carboxyl terminal end (IYAAPK-$NH_2$, (SEQ ID NO: 1)) or can be used in both forms (Ac-IYAAPK-$NH_2$, (SEQ ID NO: :1)). Because peptides show different mass spectrometric patterns, it is preferable to conduct peptides in advance so as to be suited to experimental purposes.

In still another aspect, the present invention provides a method for screening an inhibitor of enzyme activity, the method comprising the steps of: (1) reacting each of a control group consisting of a mixture of the gold nanoparticle-peptide chip of the present invention and an enzyme and of a test group consisting of the gold nanoparticle-peptide chip, the enzyme and a test substance; (2) measuring the mass of the peptide in the gold nanopeptide chip in each of the control group and the test group after completion of the reaction; (3) comparing the peptide mass of the control group with the peptide mass of the test group, measured in the step (2), to determine the effect of the test substance on the activity of the enzyme.

The characteristics of the enzyme or peptide used in the method of screening the inhibitor of enzyme activity and in the following method of quantifying enzyme activity inhibition are the same as described in the above method of detecting the activity of enzyme.

Furthermore, the method of screening the enzyme activity inhibitor according to the present invention can be applied to quantify enzyme activity inhibition. Specifically, the inhibition of enzyme activity can be quantified using a method comprising the steps of: (1) reacting a test group consisting of a mixture of the inventive gold nanoparticle-peptide chip, an enzyme and a test substance while changing the concentration of the test substance; (2) measuring the mass of the peptide in each of the gold nanoparticle-peptide chip before reaction with the enzyme and of gold nanoparticle-peptide chip of the test group having varying concentrations of the test substance after completion of the reaction; (3) calculating inhibitory activity from the ratio between a peak corresponding to the measured mass of the peptide mass before reaction with the enzyme and a peak corresponding to the measured mass of the peptide modified by the enzyme, and determining the correlation between the inhibitory activity and the concentration of an inhibitor; (4) determining the concentration of the inhibitor at which the inhibitory effects of the two peaks in the step (3) are 50%. It is possible to compare enzyme activity inhibitory effects with each other by comparing the inhibition values determined according to the inventive method between test substances.

Because the calculation method of inhibitory activity and $IC_{50}$ value for presenting a standardized method for the quantitative analysis of the measurement results of the inhibitory activity of the enzyme activity inhibitor is described in further detail in Example 4 below, a specific description of the calculation is substituted with the content of Example 4. In Examples of the present invention, only an inhibitory effect against kinase was cited as an instance, but the present invention is not limited thereto, the effects of inhibitors against various enzymatic reactions can be detected, and $IC_{50}$ value can be accurately determined through a more specific quantitative reaction process.

A plurality of species of peptides can be simultaneously bound to the gold nanoparticle-peptide chip of the present invention, such that various enzymatic activities can be simultaneously measured.

More specifically, when a chip comprising two or more peptides bound onto gold nanoparticles is used, it is possible to perform simultaneous analysis by allowing various enzymes to simultaneously react at different positions. When one enzyme has various activities, it is of course possible to perform the simultaneous analysis of the various activities. According to the above method, many peptides can be integrated, and thus the screening of various enzymatic activities can be more rapidly achieved. However, in order to bind a plurality of peptides onto gold nanoparticles, it is preferable to control the concentration of each of the peptides in a reaction solution so as to select a concentration range that can provide the same magnitude at the peptide mass peak, because there can be a difference in binding ability between the peptides due to the structures thereof.

When a number of species of peptides are simultaneously bound to gold nanoparticles, the peptides can be microarrayed or arrayed by microfluidic patterning. When a number of species of peptides are assayed on the self-assembled monolayer, enzymatic activity can be detected at high speed by comparing images before and after an enzyme reaction using mass spectrometric imaging. Unlike mass spectrometric spectra, mass spectrometry imaging techniques have advantages in that, when secondary ions generated in a specific area for a given time are acquired and information is stored, a desired mass range can be detected fast, so that the distribution of a substance having the corresponding mass in the measurement area can be accurately predicted.

Hereinafter, the present invention will be described in further detail with reference to examples. It is to be understood, however, that these examples are illustrative only, and the scope of the present invention is not limited thereto.

EXAMPLES

Example 1

Preparation of Gold Nanoparticle-Peptide Chip

A substrate comprising titanium (Ti, 20 Å) and gold (Au, 400 Å), sequentially plated on silicon, was immersed in a pirana solution of sulfuric acid/hydrogen peroxide for 5 minutes, and was then taken out of the solution and washed with distilled water.

To construct a self-assembled monolayer on the substrate, the substrate was immersed in an ethanol solution of 2 mM 11-mercaptoundecylamine (MUAM) (Dojindo) under a nitrogen atmosphere for 2 hours, and then taken out of the solution and washed with ethanol.

85 µL of an aqueous solution of 30 mM HAuCl$_4$.3H$_2$O (Aldrich) was added to 97.3 mL of pure distilled water, and the solution was stirred for 1 minute. Then, 1 mL of an aqueous solution of 1% C$_6$H$_5$Na$_3$O$_7$.3H$_2$O (trisodium salt, Sigma) was added thereto and the mixture solution was stirred for 2 minutes. After completion of the stirring, 85 µL of an aqueous solution of 300 mM NaBH$_4$ (sodium borohydride, Sigma) was added to the solution, and the solution was additionally stirred at room temperature for 10 minutes, thus preparing a gold nanoparticle dispersion. The prepared dispersion was stored at 4° C. before use. The substrate having the self-assembled monolayer formed thereon was immersed in the above-prepared gold nanoparticle dispersion for 30 minutes, and then washed with distilled water, thus forming a gold nanoparticle/self-assembled monolayer.

Peptide Ac-PRNYVTP-NH$_2$ (SEQ ID NO: 7)(Peptron Co., Ltd.) was dissolved in 10 mM phosphate buffer saline (pH 7.4) to a final peptide concentration of 50 mM and used for binding to the substrate. The gold nanoparticle/self-assembled monolayer was immersed in the peptide solution at room temperature for 1 hour, and then taken out of the solution, washed with distilled water and dried using nitrogen gas, thus preparing a gold nanoparticle-(Ac-PRNYVTP-NH$_2$ (SEQ ID NO: 7)) chip.

2) Preparation of gold nanoparticle-(Ac-PRNYpVTP-NH$_2$ (SEQ ID NO: 7)) chip

A gold nanoparticle-(Ac-PRNYpVTP-NH$_2$ (SEQ ID NO: 7)) chip was prepared in the same manner as in the above section 1), except that (Ac-PRNYpVTP-NH$_2$ (SEQ ID NO: 7)) was used instead of (Ac-PRNYVTP-NH$_2$ (SEQ ID NO: 7)) as peptide.

3) Preparation of gold nanoparticle-IYAAPKKGGGGC (SEQ ID NO: 8)) chip

A silicon substrate was immersed in a pirana solution of sulfuric acid/hydrogen peroxide for 5 minutes, and then taken out of the solution and washed with distilled water.

In order to construct a self-assembled monolayer on the substrate, the substrate was immersed in a methanol solution of 10% 3-(aminopropyl)triethoxysilane (3-APTES, Aldrich) under a nitrogen atmosphere for 2 hours, and then taken out of the solution and washed with methanol. After a gold nanoparticle/self-assembled monolayer was constructed according to the same method as in the above section 1), peptide Ac-IYAAPKKGGGGC (SEQ ID NO: 8) (Peptron Co., Ltd.) was dissolved in 10 mM phosphate buffer saline (pH 7.4) to a final peptide concentration of 50 mM and used for binding to the substrate. The gold nanoparticle/self-assembled monolayer was immersed in the peptide solution at room temperature for 1 hour, and then taken out of the solution, washed with distilled water and dried using nitrogen gas.

Polyethyleneglycol (mPEG-SMB-2000, Nektar) was dissolved in 50 mM sodium bicarbonate buffer (pH 8.5) to a final concentration of 5 mM, and the peptide-bound chip was immersed in the solution, allowed to react at room temperature for 30 minutes, washed with distilled water, thus preparing a gold nanoparticle-IYAAPKKGGGGC (SEQ ID NO: 8)) chip.

4) Preparation of gold nanoparticle-(Ac-IYAAP-KKGGGGC (SEQ ID NO: 8) +Ac-LRRASLGGGGC (SEQ ID NO: 9)) chip A gold nanoparticle-(Ac-PRNYpVTP-NH$_2$ (SEQ ID NO: 7)) chip was prepared according to the same method as in the above section 3), except that a mixture of Ac-IYAAP-KKGGGGC (SEQ ID NO: 8) and Ac-LRRASLGGGGC (SEQ ID NO: 9) was used instead of Ac-IYAAPKKGGGGC (SEQ ID NO: 8) as peptide.

5) Preparation of Gold Nanoparticle-Peptide Chip by Micropatterning

According to the process of the above section 1), a self-assembled monolayer was constructed and a dispersion of gold nanoparticles was prepared. Then, the prepared gold nanoparticle dispersion having a concentration of 250 µM was adsorbed on the monolayer surface through microfluidic channels provided in an SPR system (BIAcore-X, Sweden) for 30 minutes, and the surface was then washed with distilled water.

Then, 50 mM peptide P1 (Ac-PRNYVTP-NH$_2$ (SEQ ID NO: 7)) was introduced into channel 1 at a flow rate of about 3 µl/min for 30 minutes, after which 50 mM peptide P2 (Ac-PRNYpVTP-NH$_2$ (SEQ ID NO: 7)) was introduced into channel 2 in the same manner. Then, the surface was washed with distilled water and dried using nitrogen gas.

Herein, the width of one of the microfluidic channels was about 500 µm and the interval between the channels was 100 µm.

Example 2

Secondary Ion Mass Spectrometry of Peptide in Gold Nanoparticle-Peptide Chip

The secondary ion mass spectrometer of peptide in the gold nanoparticle-peptide chip was performed and it was observed that the secondary ion mass signal of the peptide was amplified by the gold nanoparticles. The secondary ion mass spectrometry was performed using TOF-SIMS V (ION-TOF GmbH) with Au$_1^+$ or Bi$_1^+$ primary ions (25 KeV) in static surface conditions (<$10^{13}$ ions/cm$^2$). The measured surface area was 500×500 µm$^2$, and the measurement results showed that the resolutions of peaks for CH$_1^+$, C$_2$H$_3^+$ and Au$_1^+$ were all maintained at 5,000 or higher.

Figure 1:
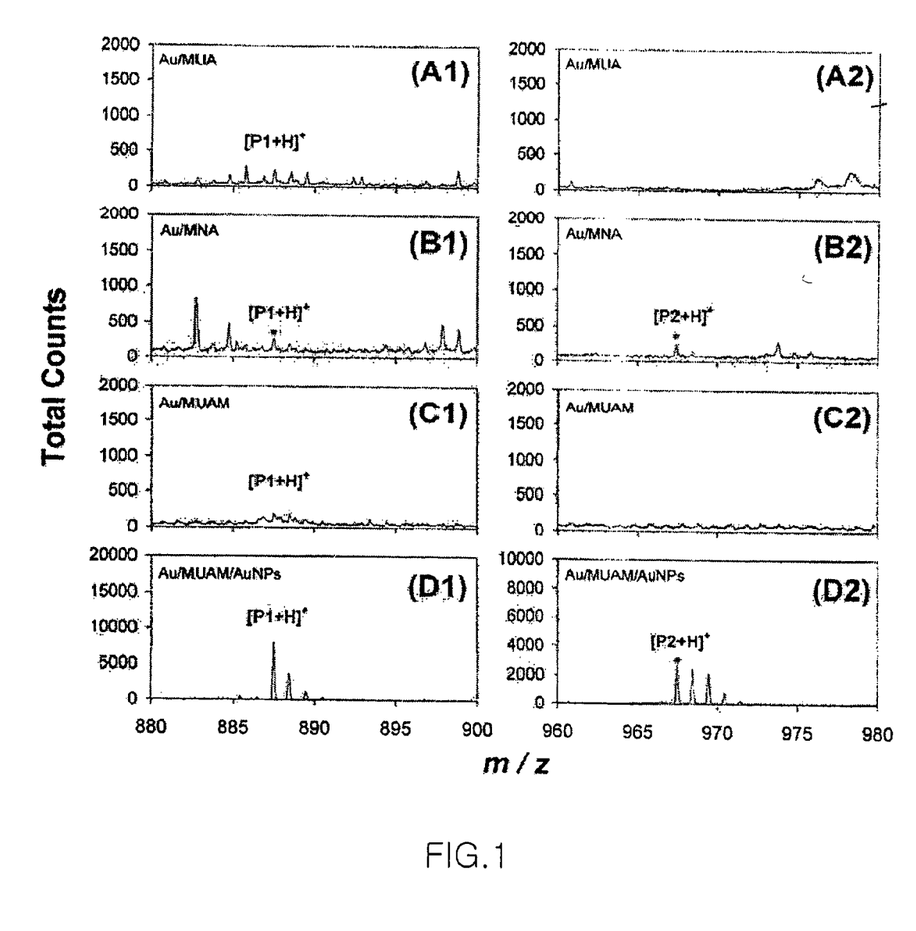
FIG. 1 shows the secondary ion mass spectrometric spectra of peptide, amplified by gold nanoparticles.

In order to compare the effects of the gold nanoparticles on the mass signal amplification of peptide, the gold nanoparticle-(Ac-PRNYVTP-NH$_2$ (SEQ ID NO: 7)) chip and gold nanoparticle-(Ac-PRNYpVTP-NH$_2$ (SEQ ID NO: 7)) chip prepared in Examples 1 and 2, respectively, together with peptide chips containing said sequences and having no gold nanoparticles, were used to perform secondary ion mass spectrometric analysis, and the analysis results are shown in FIG. 1. More specifically, the Ac-PRNYVTP-NH$_2$ (SEQ ID NO: 7) (P1) chip wherein the carboxyl terminal end was substituted with amine, and the gold nanoparticle-(Ac-PRNYpVTP-NH$_2$ (SEQ ID NO: 7)) chip having a phosphate group attached thereto, were prepared according to the same processes as in Examples 1 and 2, respectively, except that 11-mercapundecanoic acid (A1 and A2 of FIG. 1), 6-mercaptonicotinic acid (MNA) (B1 and B2 of FIG. 1) or MUAM (C1 and C2 of FIG. 1) was used to construct the self-assembled monolayer, and the process of treating the gold nanoparticle dispersion for forming the monolayer of gold nanoparticles was omitted. Also, gold nanoparticle-peptide chips (D1 and D2 of FIG. 1) having peptide together with gold nanoparticles adsorbed on MUAM were prepared. These gold nanoparticle-peptide chips were used to perform secondary ion mass spectrometric analysis, and the analysis results were compared between the gold nanoparticle-peptide chips.

In the cation spectra of secondary ion mass spectrometric analysis in FIG. 1, the major signals of the P1 and P2 peptides were detected in the form of [M+H]$^+$, and in the cases of the peptides P1 and P2, an about 10-fold increase in signals compared to the cases having no gold nanoparticles could be observed. In particular, although MNA, a self-assembled monolayer having an aromatic ring structure, was reported to be more effective in the signal amplification of secondary ions, signal amplification higher than that of MNA was observed in the gold nanoparticle-peptide chips according to the present invention.

The amount of the peptide bound on the gold nanoparticles was measured using SPR (BIAcore-X, Sweden) and, as a result, it was observed that the peptide was bound on the chips of A1, C1 and D1 in amounts of 15 ng/cm$^2$, 37 ng/cm$^2$ and 52 ng/cm$^2$, respectively, and the peptide was bound on the chip D1 in an amount about 1.4 times larger than on the chip C1 (data not shown). However, despite the fact that the peptide was bound to the self-assembled monolayer on MUA (A1) in an amount larger than on MUAM (C1), an actual signal was measured to be slightly high in MUA, suggesting that the magnitude of the mass signal of the peptide was not in proportion to the amount of the peptide. Thus, it can be considered that the effect of the signal amplification of about 10 times was not the concentration effect of the peptide, but rather was the amplification effect of the gold nanoparticles.

Example 3

Results of Secondary Ion Mass Spectrometric Measurement for Kinase Reaction

Figure 2:
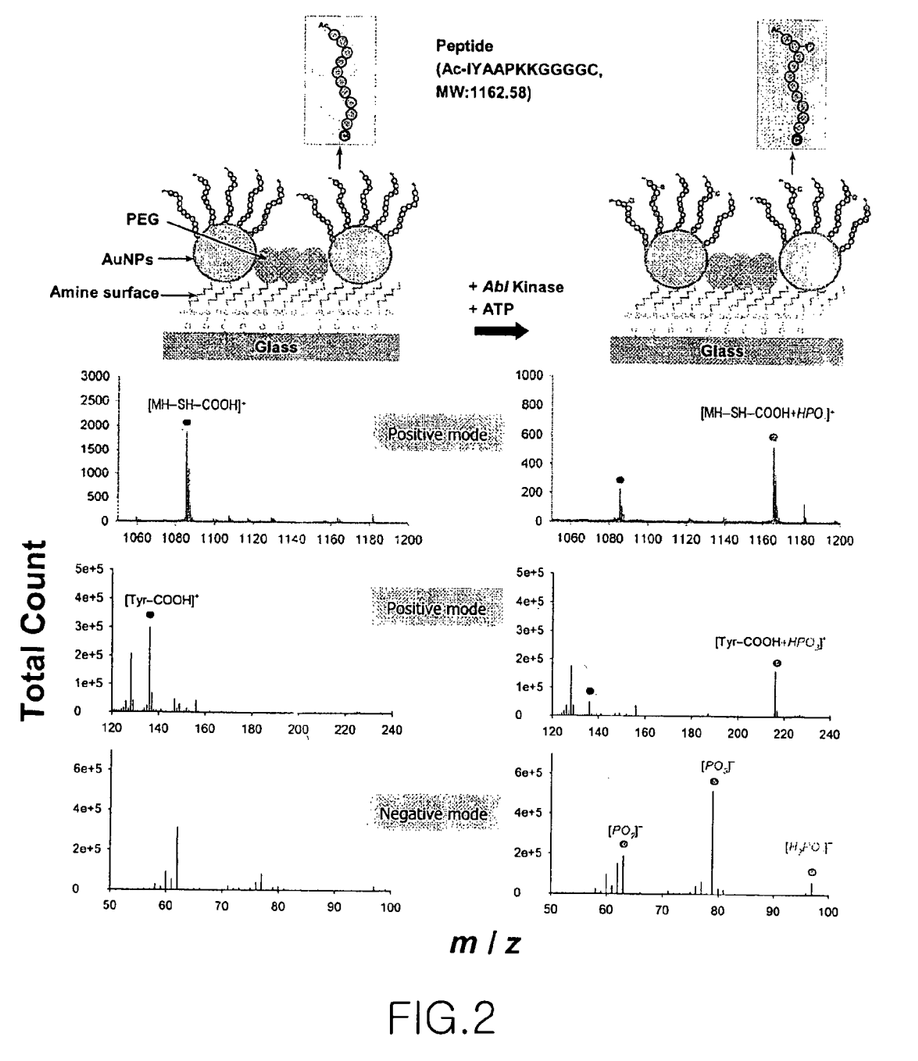
FIG. 2 shows secondary ion mass spectrometric spectra (A) before kinase reaction and secondary ion mass spectrometric spectra (B) after kinase reaction on the gold nanoparticle-based peptide chip according to the present invention.

Abl kinase (Calbiochem), ATP and MgCl$_2$ were added to 50 mM Tris buffer (containing 0.05 mM EDTA, 1 mM DTT, 0.015% Tween-20 and 0.1 mg/ml BSA, pH 7.5) to final concentrations of 2 U, 150 μM and 30 mM, respectively, to prepare a reaction solution. Then, the reaction solution was allowed to react on the gold nanoparticle-bound peptide chip prepared in Example 1-(3), at 30° C. for 2 hours. After completion of the kinase reaction, the secondary ion mass spectrometric analysis in the peptide chip was carried out in the same manner as in Example 2, and the analysis results are shown in FIG. 2. The secondary ion mass spectrometric analysis was carried out using TOF-SIMS V (ION-TOF GmbH) with an energy of 25 KeV in static surface conditions (<10$^{13}$ ions/cm$^2$) in the same manner as in Example 2, and was also carried out in an Au$_1^-$ or Bi$_1^-$ anion mode in addition to Au$_1^+$ or Bi$_1^+$ primary ions. The measured surface area was 500×500 μm$^2$ in the same manner as in Example 2, the measurement results showed that the resolutions of anion peaks for C$^-$, CH$^-$, C$_2^-$ and C$_2$H$^-$ were all maintained at 5,000 or higher.

In the cation spectra of FIG. 2, a change in mass observed in the molecular weight level of a peptide having cystein attached to the amine terminal end ([MH—SH—COOH]$^+$→[MH—SH—COOH+HPO$_3$]$^+$, and a change in mass around tyrosine ([Tyr-COOH]$^+$→[Tyr-COOH+HPO$_3$]$^+$, were detected, and in the anion spectra, phosphate ions (PO$_2^-$, PO$_3^-$ and H$_2$PO$_4^-$) were detected. Thus, it could be seen that, due to the reaction between the peptide and kinase on the gold nanoparticle-peptide chip, the phosphorylation of the peptide occurred.

This Example demonstrated that the activity of enzyme could be easily measured by measuring a change in the mass of peptide, caused by an enzymatic reaction in the gold nanoparticle-peptide chip.

Example 4

Quantitative Analysis of Inhibitory Reaction Against Kinase

As one example for analyzing an inhibitory reaction against kinase activity, the effect of 4-cyano-3-methylisoquinoline (CMIQ, Sigma), an inhibitor against PKA kinase, was illustrated.

After silicon rubber having circular holes (3 mm diameter and 1 mm height) was attached to the surface of a slide glass (75×25 mm) consisting of a glass substrate, a gold nanoparticle-peptide chip was constructed in each of the holes according to the method of Examples 1-(3).

CMIQ was dissolved in a minimum amount of distilled water to prepare solutions having varying CMIP concentrations of 0.1 nM, 0.5 nM, 1 nM, 5 nM, 10 nM, 50 nM, 100 nM, 500 nM, 1 μM and 5 μM, and each of the solutions was mixed with kinase, was introduced into the gold nanoparticle-peptide chip formed in the holes and was allowed to react at 30° C. for 2 hours. In this reaction, the concentration of ATP was 10 μM, and the concentration of kinase used was 1 U. Since the amount of the peptide attached to the surface would generally be constant, the ATP and kinase concentrations were determined as concentrations at which the maximum enzyme reaction occurred.

In order to suggest a standardized method for the quantitative analysis of measurement results, percent phosphorylation was calculated from secondary ion spectrometric spectra on the basis of the ratio between the peak area before phosphorylation of the peptide used (hereinafter, referred to as A$_{p1}$) and the peak area after phosphorylation of the peptide (hereinafter, referred to as A$_{p1}$), that is, the ratio between [MH—SH—COOH]$^+$ and [MH—SH—COOH+HPO$_3$]$^+$. The choice of the peaks before and after phosphorylation is not limited thereto, and peaks changed by phosphorylation as shown in FIG. 2 may all be applied. The peak area refers to an area at which a point corresponding to ½ of the height of a peak having the highest signal meets the mass region of the peak.

More specifically, the values of A$_{p1}$ and A$_{p2}$ in the two reference samples, that is, the gold nanoparticle-peptide chip before treatment with kinase and the gold nanoparticle-peptide chip after phosphorylation, would be different depending on the intensity of ions. Thus, to correct this difference, percent phosphorylation was calculated according to the following equation 1:

Percent phosphorylation= [Equation 1]

$$\frac{\left(A_{p2} - \frac{A_{p1} + A_{p2}}{R_1 A_{p1} + R_1 A_{p2}} \times R_1 A_{p2}\right)}{\left(A_{p2} - \frac{A_{p1} + A_{p2}}{R_1 A_{p1} + R_1 A_{p2}} \times R_1 A_{p2}\right) + \left(A_{p1} - \frac{A_{p1} + A_{p2}}{R_2 A_{p1} + R_2 A_{p2}} \times R_2 A_{p1}\right)}$$

The signs used in the equation 1 mean the areas of peaks in the secondary ion mass spectrometric spectra of each of the gold nanoparticle-peptide chips, and the detailed meanings thereof are shown in Table 1 below.

TABLE 1

|  | Mass peak area of peptide before phosphorylation | Mass peak area of peptide after phosphorylation |
| --- | --- | --- |
| Gold nanoparticle-(Ac-PRNYVTP-NH$_2$ (SEQ ID NO: 7)) chip (gold nanoparticle-peptide chip before phosphorylation) | R$_1$A$_{p1}$ | R$_1$A$_{p2}$ |
| Gold nanoparticle-(Ac-PRNYpVTP-NH$_2$ (SEQ ID NO: 7)) chip (gold nanoparticle-peptide chip after phosphorylation) | R$_2$A$_{p1}$ | R$_2$A$_{p2}$ |

TABLE 1-continued

|  | Mass peak area of peptide before phosphorylation | Mass peak area of peptide after phosphorylation |
| --- | --- | --- |
| Test sample which reacted with kinase and inhibitor | $A_{p1}$ | $A_{p2}$ |

Table 2 below shows specific examples of calculated percent phosphorylation.

TABLE 2

|  | $A_{p1}$ | $A_{p2}$ | $\dfrac{A_{p1} + A_{p2}}{R_1 A_{p1} + R_1 A_{p2}} \times R_1 A_{p2}$ | $\dfrac{A_{p1} + A_{p2}}{R_2 A_{p1} + R_2 A_{p2}} \times R_2 A_{p1}$ | Percent phosphorylation |
| --- | --- | --- | --- | --- | --- |
| Gold nanoparticle-(Ac-PRNYVTP (SEQ ID NO: 7)) chip (no kinase and no inhibitor) | 100 | 20 | (100 + 20)/(100 + 20) × 20 = 20 | (100 + 20)/(20 + 100) × 20 = 20 | 100 × (20 − 20)/{(100 − 20) + (20 − 20)} = 0% |
| Gold nanoparticle-(Ac-PRNYpVTP (SEQ ID NO: 7)) chip (no kinase and no inhibitor) | 20 | 100 | (20 + 100)/(100 + 20) × 20 = 20 | (20 + 100)/(20 + 100) × 20 = 20 | 100 ×(100 − 20)/{(20 − 20) + (100 − 20)} = 100 (%) |
| Measurement example 1 (Ac-PRNYVTP (SEQ ID NO: 7) + kinase, no inhibitor) | 20 | 40 | (20 + 40)/(100 + 20) × 20 = 10 | (20 + 40)/(20 + 100) × 20 = 10 | 100 × (40 − 10)/{(20 − 10) + (40 − 10)} = 75 (%) |
| Measurement example 2 (Ac-PRNYVTP (SEQ ID NO: 7) + kinase + inhibitor) | 40 | 20 | (40 + 20)/(100 + 20) × 20 = 10 | (20 + 40)/(20 + 100) × 20 = 10 | 100 × (20 − 10)/{(40 − 10) + (20 − 10)} = 25 (%) |

In order to calculate percent inhibition, substitution from the percent phosphorylation value calculated in the equation 1 is made. Kinase efficiency does not in fact reach 100%, and thus, when a kinase reaction shows the maximum phosphorylation level of 60% as calculated according to the equation 1, the phosphorylation level will be decreased from this point as a result of treatment with varying concentrations of an inhibitor. Thus, the calculation of percent inhibition can be performed, assuming that the inhibitory effect at a point at which the initial phosphorylation level is 60% is 0% and the inhibitory effect at a point at which the phosphorylation level is 0% is 100%. More specifically, after the phosphorylation level at each concentration of the inhibitor is calculated, percent inhibition can be calculated according to the following equation 2:

$$\% \text{ Inhibition} = \dfrac{(P\max - P)}{P\max} \times 100 \quad \text{[Equation 2]}$$

wherein Pmax represents the maximum phosphorylation level, that is, the phosphorylation level in a sample having no inhibitor, and P represents the phosphorylation level in a test sample.

Figure 3:
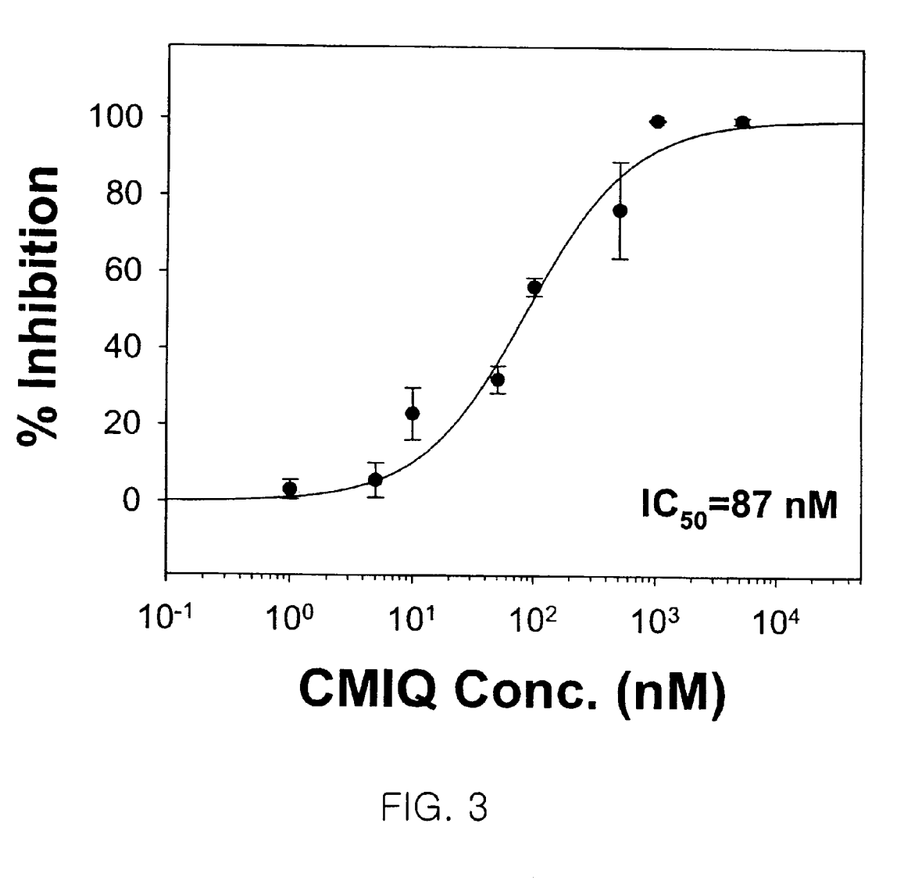
FIG. 3 is a graphic diagram showing an inhibitory effect against PKA kinase reaction on the gold nanoparticle-based peptide chip according to the present invention.

FIG. 3 shows percent inhibitions calculated according to the equation 2, when the test sample is treated with varying concentrations of the inhibitor (CMIQ) against PKA kinase. In FIG. 3, percent inhibition is shown as a variable on the x-axis, and the concentration of the inhibitor is shown as a variable on the y-axis. The correlation between percent inhibition and inhibitor concentration can be formulated from experimental data by Sigmaplot 9.0 (Systat Software Inc.) through non-linear regression using the following equation 3. From this formulation, $IC_{50}$ value (inhibitory concentration at which the maximum inhibition reaches 50%) and Imax value (percent inhibition at which the maximum inhibitory effect of the inhibitor occurs) can be calculated (Nucleic acid 2004, 32. (2), 422-431).

$$\text{Percent inhibition} = I\max \times (\text{Inhibitor concentration})^n / ((\text{Inhibitor concentration})^n + (IC_{50})) \quad \text{[Equation 3]}$$

In the case of the inhibitory effect of CMIQ against PKA kinase in this Example, Imax was 100%, n was 0.9996, and $IC_{50}$ was about 87 nM.

When this method is used, inhibitory effects against various enzyme reactions in addition to the kinase reaction can be detected, and $IC_{50}$ value can be accurately determined through a more specific quantitative reaction process.

Example 5

Multiple Analysis of Kinases

A multiple analysis of reacting specific kinases simultaneously at different locations using a chip comprising two or more peptides bound on gold nanoparticles was attempted.

Figure 4:
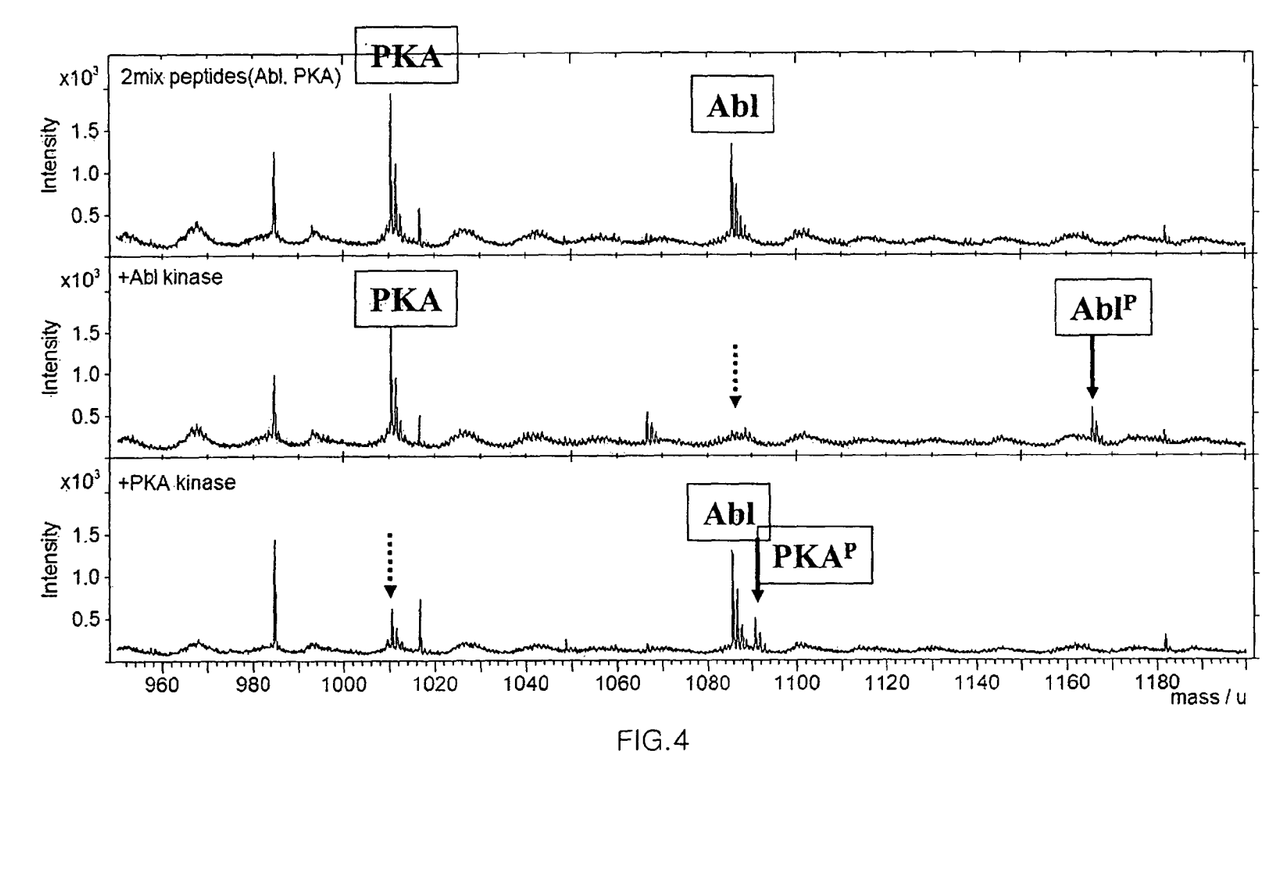
FIG. 4 shows mass spectrometric spectra illustrating the simultaneous analysis of kinase activities, performed using a gold nanoparticle-based peptide chip comprising two or more peptides bound on the gold nanoparticles.

According to the method of Example 1-(4), a gold nanoparticle-peptide chip was prepared by combining Ac-LR-RASLGGGGC (SEQ ID NO: 9) ($P_{PKA}$) and Ac-IYAAP-KKGGGGC (SEQ ID NO: 8) ($P_{Abl}$), peptides specific for PKA and Abl kinases. Each of the Abl kinase and the PKA kinase was allowed to react on the surface of the gold nanoparticle-peptide chip in the conditions described in Examples 2 and 3, and then the secondary ion mass spectrometric analysis thereof was carried out. The analysis results are shown in FIG. 4. As can be seen in FIG. 4, the Abl kinase and the PKA kinase did not influence the mass peaks of other peptides, suggesting that only the mass signals of peptides specific for the kinases were changed.

Accordingly, when this method is used, many peptides can be integrated, and thus the screening of various enzyme activities can be determined faster.

Example 6

Secondary Ion Mass Spectrometric Imaging for Kinase and Inhibitory Assay

Figure 5:
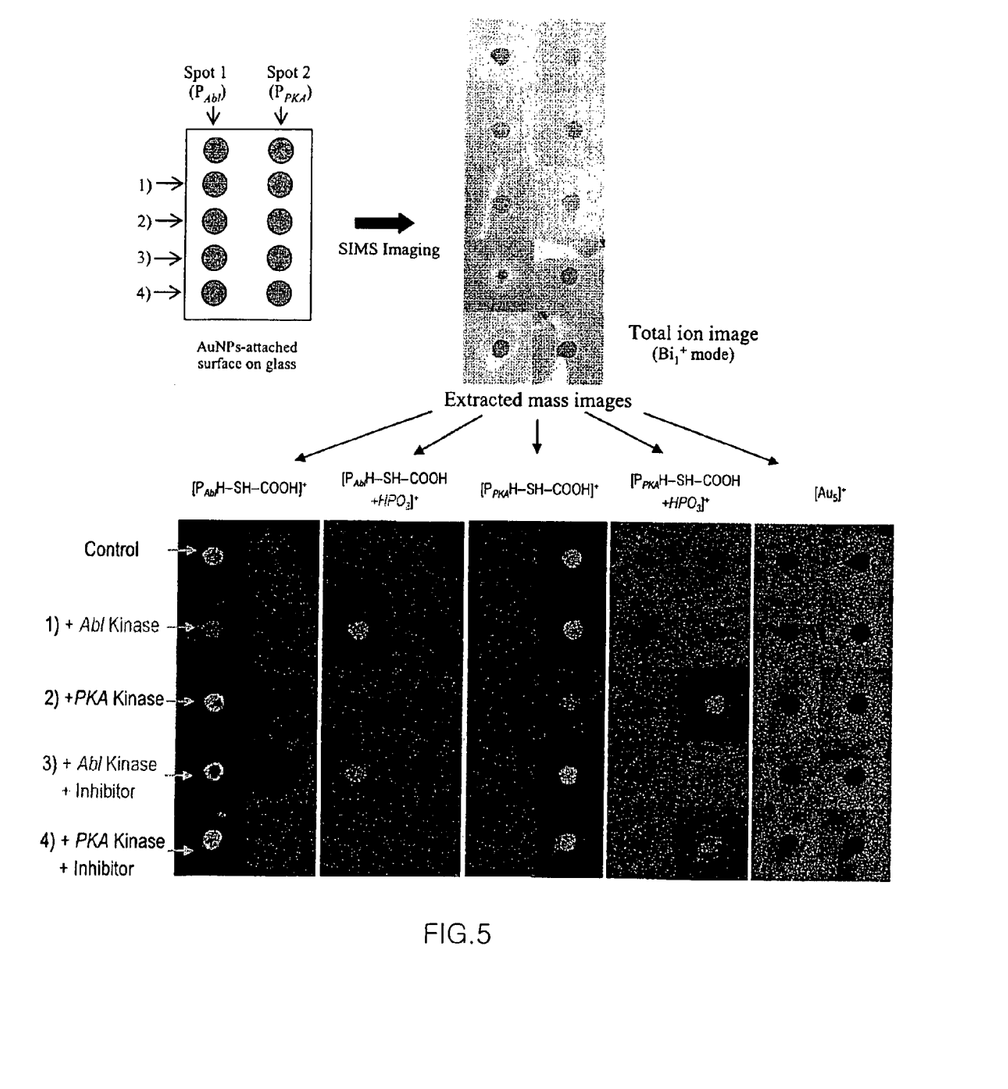
FIG. 5 illustrates a conceptual diagram and the secondary ion mass spectrometric imaging for kinase and inhibitory assay, which was obtained by using microarraying.

For the kinase assay by SIMS imaging, two peptides ($P_{Abl}$ and $P_{PKA}$) were independently spotted onto the AuNPs-attached glass surface by using a microarrayer (Microsys, Cartesian Technologies, Irvine, Calif., USA) (spot1 and spot2, FIG. 5). The peptide was dissolved in 10 mM PBS (pH 7.4) containing 5% glycerol (v/v) to give a final concentration of 50 μg mL$^{-1}$. A 10 μL reaction mixture containing either 2 nM Abl or 50 nM PKA with 100 μM ATP was added to each spot area, and followed by the incubation at 30° C. for 60 min. Inhibitor-containing kinase solutions (stautosporin or CMIQ, final conc. ~10 μM) were compared under same conditions. Spotting areas onto the glass surface were subjected to SIMS imaging immediately after washed with distilled water.

As shown in FIG. 5, mass change in kinase reaction was distinctly revealed by SIMS chemical imaging. Control surface without kinase reaction yielded no quasi-molecular ion images at phosphorylated mass region, whereas kinase-treated spots (line 1 and 2) yielded strong ion mass images (i.e. $[P_{Abl}H—SH—COOH+HPO_3]^+$ or $[P_{PKA}H—SH—COOH+HPO_3]^+$) with the decline of image intensities at an original peptide ion mass (i.e. $[P_{Abl}H—SH—COOH]^+$ or $[P_{PKA}H—SH—COOH]^+$). Addition of inhibitor dramatically reduced the intensity of ion mass images (line 3 and 4). No cross-images of kinases against opposite peptides were observed, and the $[Au_5]^+$ image, a gold ion signal, strongly represents that AuNPs are obviously present on the glass surface. It was also possible to perform multiplexing SIMS images by a mixture of two peptides for the detection of phosphorylation (data not shown). This result indicates that SIMS-based chemical imaging enabled the kinase assay with high specificity because all chemical ion images with a differing mass can be collectively extracted from a single measuring image. SIMS is known to provide a greater resolving sensitivity in chemical imaging than MALDI.

As described above, the gold nanoparticle-based peptide chip of the present invention makes it easy to assay kinase and inhibitory effect by detecting the mass change of the peptide.

Thus, when the gold nanoparticle-based peptide chip is applied, it is possible to perform accurate quantitative and qualitative analysis for an enzyme reaction without using any marker.

Also, the AuNP-based peptide chip can be advantageously applied for the screening of various inhibitors against specific enzymes and the development of drugs. In addition, when various peptide arrays and secondary ion mass spectrometric imaging techniques are used, the AuNP-based peptide chip can achieve the ultrahigh-speed screening of enzyme or protein activity, and thus can be widely used for the elucidation of the interactions between biomolecules, the understanding of intracellular signaling mechanisms, the diagnosis of diseases and the development of therapeutic drugs.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A method for detecting the activity of a tyrosine kinase, comprising the steps of:
   (1) measuring a mass of a peptide on a gold nanoparticle-based (AuNP-based) peptide chip by secondary ion mass spectrometry;
   (2) allowing the AuNP-based peptide chip to react with the tyrosine kinase to be measured for its activity;
   (3) measuring the mass of the peptide on the AuNP-based peptide chip after reacting with the tyrosine kinase by secondary ion mass spectrometry; and
   (4) measuring the change between the peptide mass measured in step (1) and the peptide mass measured in step (3) to determine the activity of the tyrosine kinase, wherein the AuNP-based peptide chip comprises:
   a glass support;
   a self-assembled monolayer constructed on the support using 11-mercaptoundecylamine (MUAM);
   a monolayer of gold nanoparticles (AuNPs) formed on the self-assembled monolayer by binding between the self-assembled monolayer and the AuNPs; and
   a peptide immobilized by the AuNPs; and
the peptide on the AuNP-based peptide chip having a length expanded through a glycine linker, wherein the amino-terminal end of the peptide on the AuNP-based peptide chip is cysteine.

* * * * *

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Tyr Ala Ala Pro Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Tyr Ala Ala Pro Lys Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ile Tyr Ala Ala Pro Lys
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Tyr Ala Ala Pro Lys Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Tyr Ala Ala Pro Lys Arg
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ala Ala Pro Lys Gly Gly Gly Gly Cys
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Arg Asn Tyr Val Thr Pro
1               5

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Tyr Ala Ala Pro Lys Lys Gly Gly Gly Gly Cys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 9

Leu Arg Arg Ala Ser Leu Gly Gly Gly Gly Cys
1               5                   10